(12) United States Patent
Williams

(10) Patent No.: US 7,805,772 B2
(45) Date of Patent: Oct. 5, 2010

(54) AUTOMATIC GLOVING MACHINE AND METHOD AND GLOVE PACKAGE FOR USE THEREWITH

(76) Inventor: Llewellyn Angelo Williams, 22 Clinton Ave., New Rochelle, NY (US) 10801

( * ) Notice: Subject to any disclaimer, the term of this patent is extended or adjusted under 35 U.S.C. 154(b) by 1377 days.

(21) Appl. No.: 11/233,926

(22) Filed: Sep. 23, 2005

(65) Prior Publication Data
US 2006/0144878 A1 Jul. 6, 2006

Related U.S. Application Data

(60) Provisional application No. 60/612,940, filed on Sep. 24, 2004.

(51) Int. Cl.
*A47G 25/80* (2006.01)
(52) U.S. Cl. .......................................................... 2/111
(58) Field of Classification Search .......... 223/111–119
See application file for complete search history.

(56) References Cited

U.S. PATENT DOCUMENTS

| | | | | |
|---|---|---|---|---|
| 4,449,911 A | * | 5/1984 | Brasfiel | 425/374 |
| 5,058,785 A | * | 10/1991 | Rich et al. | 223/111 |
| 5,975,083 A | * | 11/1999 | Henderson, Jr. | 128/878 |
| 6,168,019 B1 | * | 1/2001 | Olson | 206/390 |
| 6,360,373 B1 | * | 3/2002 | Rehn et al. | 2/161.6 |
| 6,375,034 B1 | * | 4/2002 | Corbett | 221/46 |
| 6,832,708 B2 | * | 12/2004 | Sinai | 223/111 |
| 2005/0066413 A1 | * | 3/2005 | Mattesky | 2/161.6 |
| 2005/0155133 A1 | * | 7/2005 | Sato | 2/159 |
| 2007/0170213 A1 | * | 7/2007 | Gaines et al. | 223/111 |

\* cited by examiner

*Primary Examiner*—Shaun R Hurley
*Assistant Examiner*—Andrew W Sutton
(74) *Attorney, Agent, or Firm*—Dorsey & Whitney LLP

(57) ABSTRACT

A method and apparatus for gloving a person and a gloving package. The method includes automatically advancing a glove package or packages containing gloves from a storage location to a location where they are accessible to a persons hands so that the person can glove himself or herself without contaminating the gloves. The apparatus comprises of a gloving machine for applying gloves to the hands of a person. The gloving package is comprised of a top and bottom layer and a means for securing glove(s) within the layers.

10 Claims, 13 Drawing Sheets

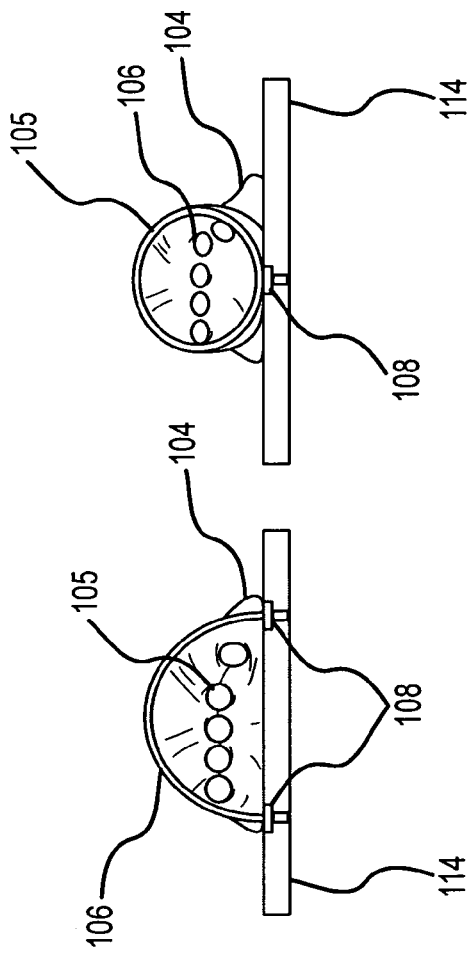
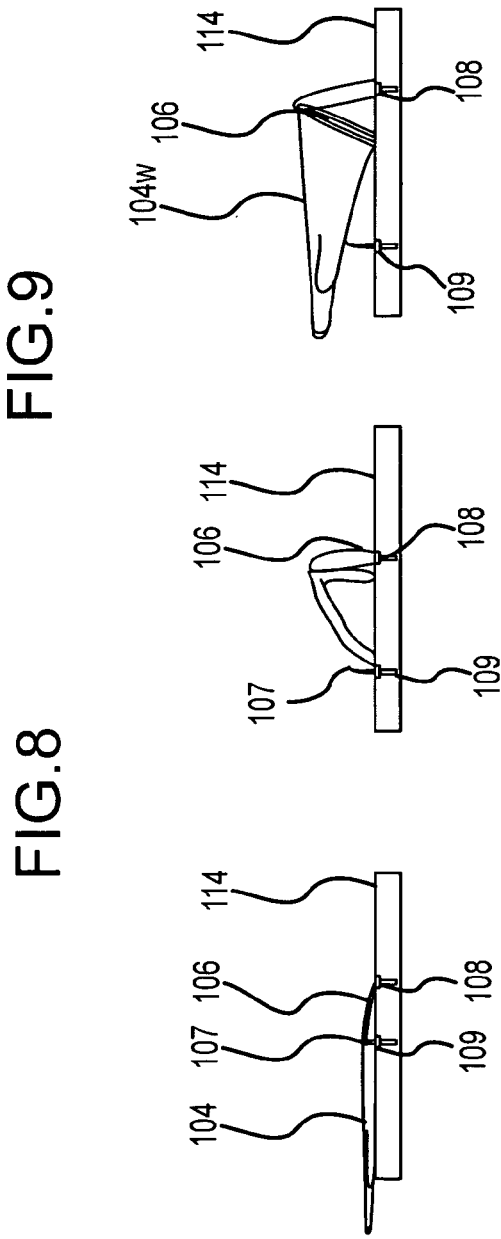

AUTOMATIC GLOVING MACHINE AND METHOD AND GLOVE PACKAGE FOR USE THEREWITH

RELATED APPLICATIONS

This application is related to and claims the benefit of priority under 35 U.S.C. 120 and/or 35 U.S.C. 119 to U.S. Provisional Patent Application No. 60/612,940 filed on 24 Sep. 2004 and entitled Automatic Gloving Machine And Method And Glove Package For Use Therewith, which application is incorporated herein by reference.

FIELD OF THE INVENTION

This invention relates generally to an apparatus and a method of gloving a user's hands for users in various fields and to a packaged glove or gloves for use with the apparatus or method.

BACKGROUND

Gloves have been used in a variety of settings as a barrier between the hands of users and objects. One example of common usage for gloves is in clean room environments. Generally, these gloves undergo a special washing and cleaning process in order to remove particulate matters along with other contaminants, so they don't contaminate products and product environments. These gloves are also packaged in a clean room setting to accommodate and ensure cleanliness when received by users.

Gloves are also used in other settings, such as in the medical field. Gloves in this environment are designed to protect both patients and healthcare workers from spreading germs. They are used to protect the hands of surgical operators, medical examiners, staff, and patients from harsh infections that can be transferred during these processes.

Surgical and examination gloves are essential in the medical environment because they act as a barrier, providing separation between a patient and health care worker. In this capacity, gloves act to block the introduction of infectious agents, particularly bacteria and fungi, from the hands of the healthcare worker into a surgical incision or wound of the patient.

It has been recognized that bacteria present in pores of healthcare workers hands frequently survive the cleaning prior to the gloving procedure and thus are transported to the glove during the gloving process.

Currently, there are different techniques available for putting on sterile or clean gloves. Based on these techniques, the user must pick up the first glove by the cuff, touching only the inside portion of the cuff (the inside is the side that will be touching the user's skin when the glove is on). While holding the cuff in one hand, the user slips the other hand into the glove.

The current techniques available for putting on gloves have many limitations. In the task of putting on the glove, the user has to handle the glove, which can often result in contamination of the glove and infection of another person. Often, the process of gloving has to be repeated to ensure gloves are put on without contamination if the outer surface of the glove is touched by a bare hand during the gloving process. In addition, some of the current methods and procedures for using latex gloves recommend double gloving to reduce the contacts made to the outer portion of the glove. A user can replace the outer glove without touching the glove since he has worn a first layer glove. This method is not ideal since it adds to the cost and time involved in the gloving process.

A new method of gloving is therefore needed to alleviate the present problem of putting on gloves. The current methods are time consuming and more importantly, prone to contamination. A new method is required in order to guarantee with certainty that users will not come into physical contact with the outer shell of the glove, and thus, will not infect others.

SUMMARY OF THE INVENTION

A first aspect of the present invention provides a method of dispensing gloves and gloving a person. In one embodiment the invention provides a gloving machine for dispensing at least one glove (but more usually a pair of gloves) and applying the glove or gloves to the hands of a person where in the gloving machine includes a gloving region having a surface for supporting a packaged glove to a person, the gloving region accessible to the hand of the person to be gloved; a glove package storage region for storing a plurality of packaged gloves; and a glove package transport mechanism operative to retrieve at least one glove enclosed in a substantially sealed glove package from the storage region to the gloving region.

In another one embodiment the invention provides a method for dispensing gloves and gloving a person that includes the steps of advancing a new package containing a glove or pair of gloves, including a first glove and a second glove, attached to a web of material for transporting the package from a normally inaccessible storage location to a user accessible location within the housing of a gloving machine. The package is opened as it is advanced through the gloving machine by removing an upper cover layer of material from the first and second gloves and from a lower base layer of material. A first glove and a second glove are presented on the lower base layer and directs the glove to within arms reach of the person to be gloved. Both gloves are stabilized in such a position on the gloving surface so that the person can insert a first and a second hand into an opening in the first and second glove without needing to touch or hold the outer surface of either glove and then permitting detachment of the first and second gloves from the lower base layer of material to complete the gloving operation.

In another aspect, the invention provides a gloving machine for applying gloves to the hands of a person. The gloving machine may be manually activated or motorized.

In another aspect, the invention provides a gloving package that is comprised of a substantially planar sheet that forms the bottom package layer and a glove pair including a first and second glove arranged in a side-by-side relationship. This invention also provides a means for securing the glove pair to the bottom package layer. A substantially planar sheet forms the top package layer, overlaying the glove pair and securing or sealing the top layer to the bottom package layer to contain the glove pair and maintain a desired degree of sanitation or sterility.

The inventive glove dispensing machine and gloving apparatus may be implemented in a variety of physical sizes and shapes to suit the volume of gloves to be dispensed and the space available. Floor-standing, table-top, shelf-mounted, and wall-mounted versions of the gloving machine may be provided.

BRIEF DESCRIPTION OF THE DRAWINGS

FIG. 8 is an illustration showing an embodiment of a glove with a partial-loop or partial-hoop supportive glove-opening attachment strip and dual-fasteners.

FIG. 9 is an illustration showing an embodiment of a glove with a full-loop or full-hoop supportive glove-opening attachment strip and a single fastener.

FIG. 10 is an illustration showing an embodiment of structure and method for retaining the glove, where FIG. 10a shows the glove in a latched configuration, FIG. 10b shows the glove as the latch is being released, and FIG. 10c shows the glove in an open configuration.

FIG. 11 is an illustration showing an embodiment of the glove package assembly showing the separation of the upper layer from the glove or gloves and the lower layer, where

DETAILED DESCRIPTION OF EMBODIMENTS OF THE INVENTION

Various embodiments of the invention are now described that illustrate exemplary structures and machines as well as methods for gloving and glove or gloves packages that may advantageously be used with the gloving machines or separately in other gloving machines. It will be appreciated that although both floor-standing and table-top models are shown and described, the structure and operating principles disclosed are applicable to gloving machines or any size and physical configuration.

In one embodiment, the gloving machine is a table-top or counter-top model suitable for restaurant or food service operation and can fit within a foot print of no greater than about 2 feet×2 feet×2 feet. Other embodiments may occupy less space while still other floor-standing embodiments may require a foot print from about 2 feet to about 4 feet on a side. Those workers having ordinary skill in the mechanical arts will appreciate that the gloving machine may be any physical size that permits the storage (when stored internal to the machine) and transport of the packaged gloves from a storage region to a gloving region large enough for the gloving operation to be performed, and then removal of the empty glove packaging material. In embodiments that store the packaged gloves and/or empty glove packaging material external to the housing of the gloving machine, the size of the gloving machine may be reduced to only that required to transport the gloves to the users hand for the glove dispensing and or gloving operation to be performed.

In some environments where there may exist a need for a large volume of gloves to be dispensed over a short period of time, or dispensed over a longer period of time with fewer service calls to refill the machine, lager floor standing or wall mounted machines may be desirable. In other environments, such as in medical clinics, hospitals, restaurants, automotive repair shops, or other business establishments, there may be an advantage to a smaller table top or portable unit, or to a smaller wall mounted or mountable unit. It will be appreciated in light of the description provided herein, that the mechanical wheels, gears, pulleys, belts, motors, and other mechanical components (glove transport mechanics) may be scaled in dimension to suit the overall machine size desired. Furthermore, different assemblies of glove transport mechanics may be substituted to perform the glove transport functions described relative to particular embodiments, so that the invention is not limited only to the particular embodiments described herein.

Figure 1:
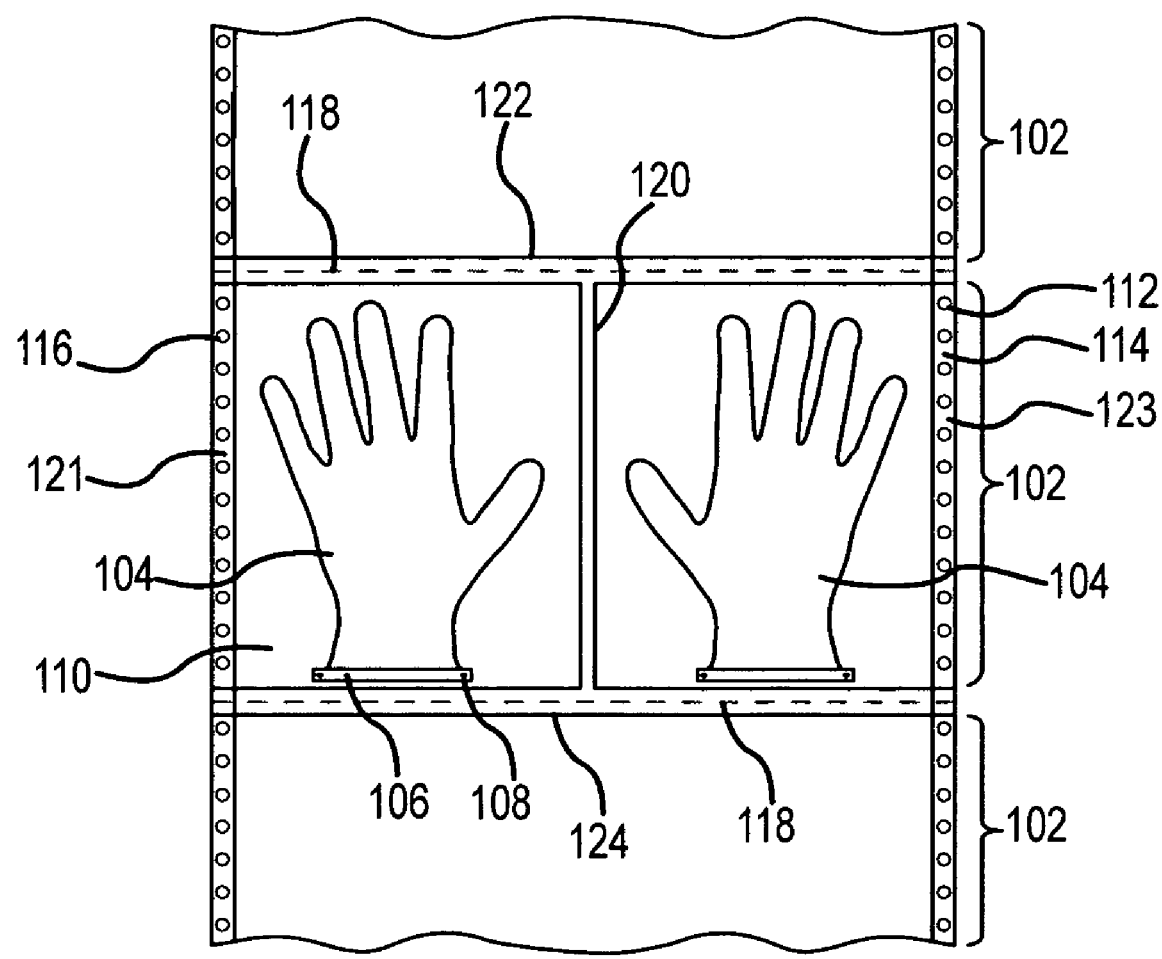
FIG. 1 is an illustration showing an embodiment of a packaged two-glove assembly in roll or pleated form.

FIG. 1 shows an embodiment of a packaged two-glove assembly that may be stored in a roll or pleated/folded form. Folded or pleated forms may be advantageous for thicker gloves as there may be a tendency for such rolled packages not to roll uniformly because the assembled glove units do not have a uniform thickness unless some fill (such as paper, foam, plastic, or a pattern or array of layer separating standoffs) is utilized in the package to provide an acceptably uniform thickness for rolling. Even though non-uniform thickness packages present some challenges for rolling, it will be appreciated in light of the description provided here, that even non-uniform thickness glove packages may be rolled.

The illustrated embodiment of the glove pair packet roll 100 includes a glove pair individual packet 102 (or in an alternate embodiment, a single glove individual packet 134). The plurality of glove pair individual packets are defined along a substantially continuous web or roll of material by glove pair roll tear perforations 118. Various seals may be provided to attach upper and lower layers of packaging material and they may be joined or adhered by seals to protect the integrity of the package when desired, such as to maintain the gloves 104 in a clean, hygienic, or sanitary condition from the time of assembly until applied to the hands of a wearer. These seals may be formed using an adhesive, an acoustic welding, pressure, or any other known attachment method for attaching sheets or layers of material together. The adhesion should be such that the integrity of the package 102 is maintained during transport of the rolled or pleated material 100 and storage in or separate from the machine, but should not be so strong as to prevent separation of the layers as the layers are separated by the machine during a gloving operation. (The gloving operation and the manner in which the package is opened and separated according to one embodiment of the invention is described in detail hereinafter.)

A glove pair center seal 120 extends substantially between right and left gloves 104, but is optional in that the two gloves are enclosed by four surrounding seals including glove pair packet leading edge seal 122, glove pair packet trailing edge seal 124, glove pair packet left edge seal 121, and glove pair packet right edge seal 123. The leading edge is referenced to the first portion of the material 100 to unroll or unfold from storage and be presented to the glove wearer, and the trailing edge portion is referenced to the portion that unrolls or unfolds subsequently. Optional perforations or other gripping or traction means 116 are provided along one or both lateral edges of the web 100 and may be used to assist transport of the web 100 through the machine. Depending upon the thickness of the layers, the type of transport, and other factors, the perforations may extend through one, more than one, or all of the layers. In one embodiment, the perforations extend through the upper, fill, and lower layers. In another embodiment, a plastic bead or chain having a series of projections is used to assist transport rather than perforations. Embodiments of the invention may alternatively pull or otherwise transport the packages 102 without these perforations, gripping means, or traction means, such as by using a belt separate from the upper and lower layers that will permit pulling without damaging the packages. Various transport and control structures and methods are known in the art for moving a web of material between two rolls so as to move the web of material without exceeding defined tension parameters. These structures and techniques may be applied to the web 100 alone or in conjunction with an additional supporting transport web.

An optional glove pair glove surround 110 may be provided that carries the glove or gloves and is a remnant of the glove fabrication process, or it may be a filler that assists at maintaining a relatively uniform package thickness between the glove containing regions and the non-glove containing regions, or may be provided to stiffen or otherwise support the gloves during transport through the machine or during a gloving operation.

According to one embodiment of the invention, the gloves are attached to the carrying web of material, such as the glove pair top package layer 112 or glove pair bottom package layer 114, or when present, surround layer 114 by an attachment strip 106 and fastener(s) 108.

Embodiments of the invention may provide that the glove pair top package layer 112 or glove pair bottom package layer 114 are made of a material such as a paper material, a plastic or polymeric material, a woven material, a coated paper or plastic material, or any combination of these. It will be appreciated that the different layers may be made of the same or different materials, and that the thickness of the materials may be independently selected to provide the desired physical properties for movement through the gloving machine.

This structure is repeated for each of the individual packages 102 along the web of upper and lower layers of material.

Figure 2:
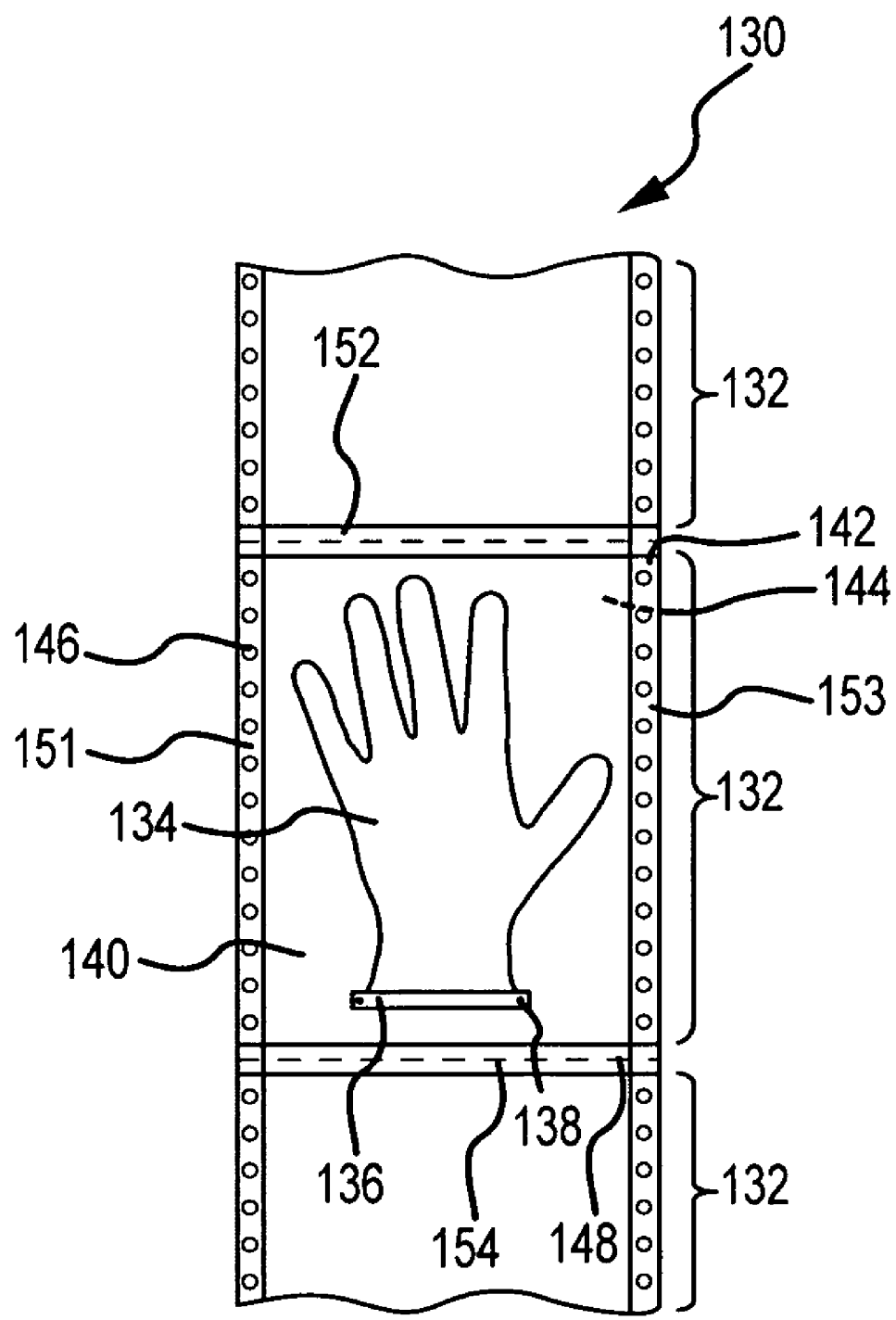
FIG. 2 is an illustration showing an embodiment of a packaged single-glove assembly in roll or pleated form.

FIG. 2 shows an embodiment of a packaged single-glove assembly 132 in roll or pleated form 130. This package is similar to that described relative to FIG. 1, except that it only contains a single glove 134 rather than a pair of gloves and the optional center seal 120 is not used because there are no gloves to separate. In one embodiment, two gloves may be provided in this package 132 in an overlaying manner, but this is not normally the preferred implementation because it requires the wearer to separately handle the gloves during a gloving operation. The illustrated embodiment of a packaged single-glove 132 or a roll or a pleated form 130 are defined along a substantially continuous web or roll of material by glove roll tear perforations 148. Various seals may be provided to attach upper and lower layers of packaging material that may be joined or adhered by seals to protect the integrity of the package when desired, such as to maintain the glove 134 in a clean, hygienic, or sanitary condition from the time of assembly until applied to the hands of a wearer. Seals may not be required or used where a sanitary or sterile condition is not required, such as in dispensing gloves for use in the automotive repair or servicing industry. These seals may be formed using an adhesive, an acoustic welding, pressure, or any other known attachment method for attaching sheets or layers of material together. The adhesion should be such that the integrity of the package 132 is maintained during transport of the rolled or pleated material 130 and storage in or separate from the machine, but is not so strong as to prevent separation of the layers, as the layers are separated by the machine during a gloving operation (the gloving operation and the manner in which the package is opened and separated according to one embodiment of the invention is described in detail hereinafter).

In the illustrated embodiments, the glove is enclosed by four surrounding seals including single glove packet leading edge seal 152, single glove packet trailing edge seal 154, single glove packet left seal 151, and single glove packet right edge seal 153. The leading edge is referenced to the first portion of the material 130 to unroll or unfold from storage and be presented to the glove wearer, and the trailing edge portion is referenced to the portion that unrolls or unfolds subsequently. Optional perforations, protuberances, ridges, or other gripping or traction means 146 are provided along one or both lateral edges of the web 130 and may be used to assist transport of the web 130 through the machine. Depending upon the thickness of the layers, the type of transport, and other factors, the perforations or other gripping or traction means may extend through one, more than one, or all of the layers. We refer to perforations in the following descriptions but by this term we mean any type of traction or gripping means that permit or facilitate moving the web through the gloving machine. In one embodiment, the perforations extend through the upper, fill, and lower layers. In another embodiment, a plastic bead or chain having a series of projections is used to assist transport rather than perforations. Embodiments of the invention may alternatively pull or otherwise transport the packages 132 without these perforations, gripping means, or traction means, such as by using a belt separate from the upper and lower layers that will permit pulling without damaging the packages. Various transport and control structures and methods are known in the art for moving a web of material between two rolls so as to move the web of material without exceeding defined tension parameters. These structures and techniques may be applied to the web 130 alone or in conjunction with an additional supporting transport web. Perforations or other gripping or traction means may be provided continuously or intermittently, and may be present on one side or edge, both sides or edges, or at an intermediate location relative to the two sides or edges of the web.

An optional single glove surround 140 may be provided that carries the glove or gloves and is a remnant of the glove fabrication process, or it may be a filler that assists at maintaining a relatively uniform package thickness between the glove containing regions and the non-glove containing regions, or may be provided to stiffen or otherwise support the gloves during transport through the machine or during a gloving operation.

According to one embodiment of the invention, the gloves are attached to the carrying web of material, such as glove pair top package layer 142 or glove pair bottom package layer 144, or when present, surround layer 144 by an attachment strip 136 and fastener(s) 138.

Embodiments of the invention may provide that the single glove top package layer 142 or single glove bottom package layer 144 are made of a material such as a paper material, a plastic or polymeric material, a woven material, a coated paper or plastic material, or any combination of these. Multiple layers of divers materials may be used. It will be appreciated that the different layers may be made of the same or different materials, and that the thickness of the materials may be independently selected to provide the desired physical properties for movement through the gloving machine.

This structure is repeated for each of the individual packages 142 along the web of upper and lower material.

Figure 3:
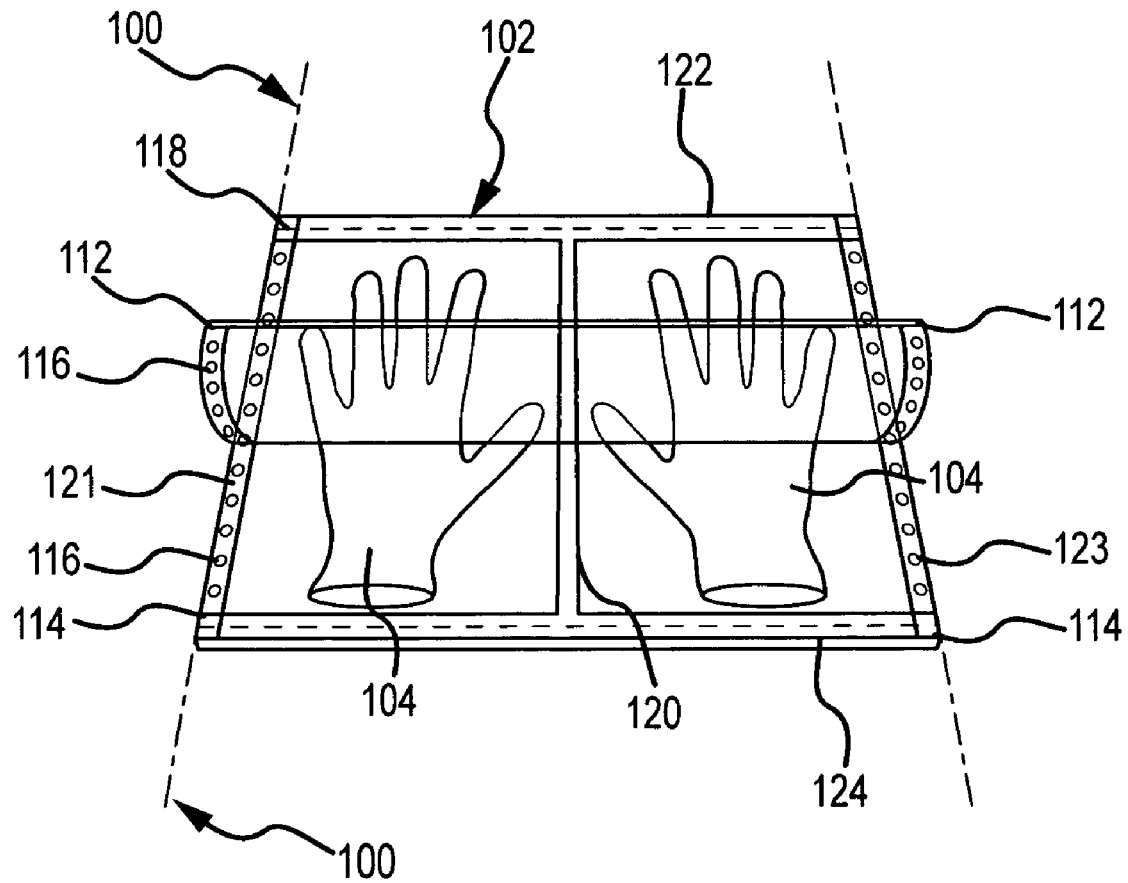
FIG. 3 is an illustration showing an embodiment of the assembly in FIG. 1 showing partial separation of the upper layer from the rest of the package.

FIG. 3 shows an embodiment of the assembly in FIG. 1 and partial separation of the upper layer from the rest of the package to illustrate the vertical layering of the glove pair individual packet 102. Only one glove pair individual packet 102 of the plurality of the units on the web 100 are shown. Where appropriate individual packet transport is provided. Separate packages 102 may be separately transported and presented for gloving without attachment to a web of material. In yet another embodiment, the packages may be supported as or on a web of material, but separated prior to the gloving operation. It will be understood that individual packages containing single or multiple gloves or glove pairs may be provided as separate unit, rather than as part of a rolled or pleated assembly, and that such individual glove packages may be dispensed manually or using different individual package dispensing machines.

This figure illustrates a glove pair top package layer 112 which is partially separated by the gloving machine during a gloving operation and hence gloves become available after a complete cycle for a user during a gloving operation. (The gloving operation and the manner in which the package is opened and separated according to this and other embodiment of the invention are described in detail hereinafter.)

Figure 4:
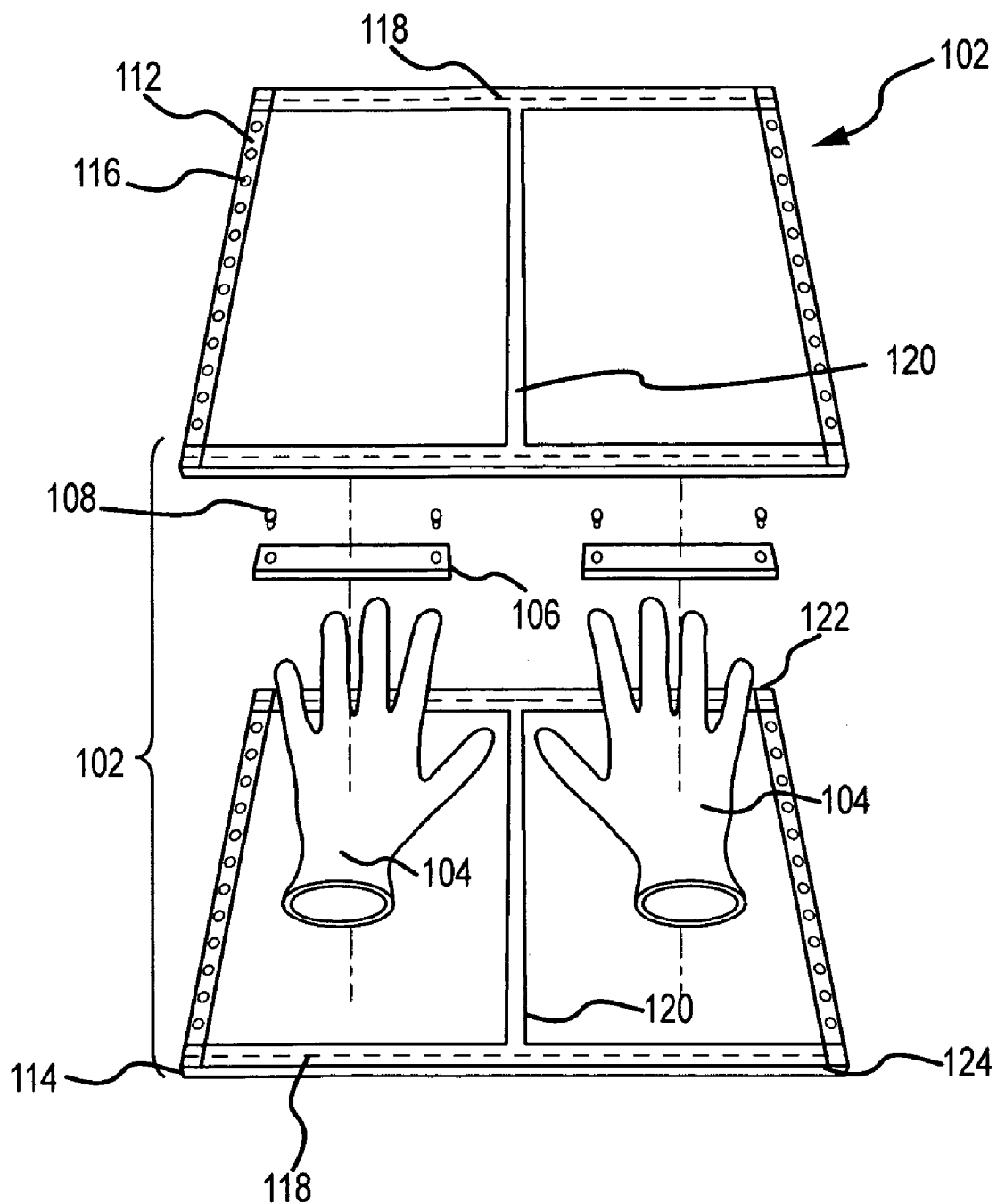
FIG. 4 is an illustration showing an embodiment of the assembly of FIG. 3 showing an exploded view of the packaged two-glove assembly.

FIG. 4 shows an embodiment of the assembly in FIG. 1 with different layers shown as an exploded view and separated to illustrate the vertical layering of the glove pair individual packet 102. Glove pair top package layer 112 is separated showing the fasters 108 and attachment strip 106 located below the glove pair top package layer 112 for fastening and attaching the glove onto the glove pair bottom package layer 114 for a gloving operation.

Figure 5:
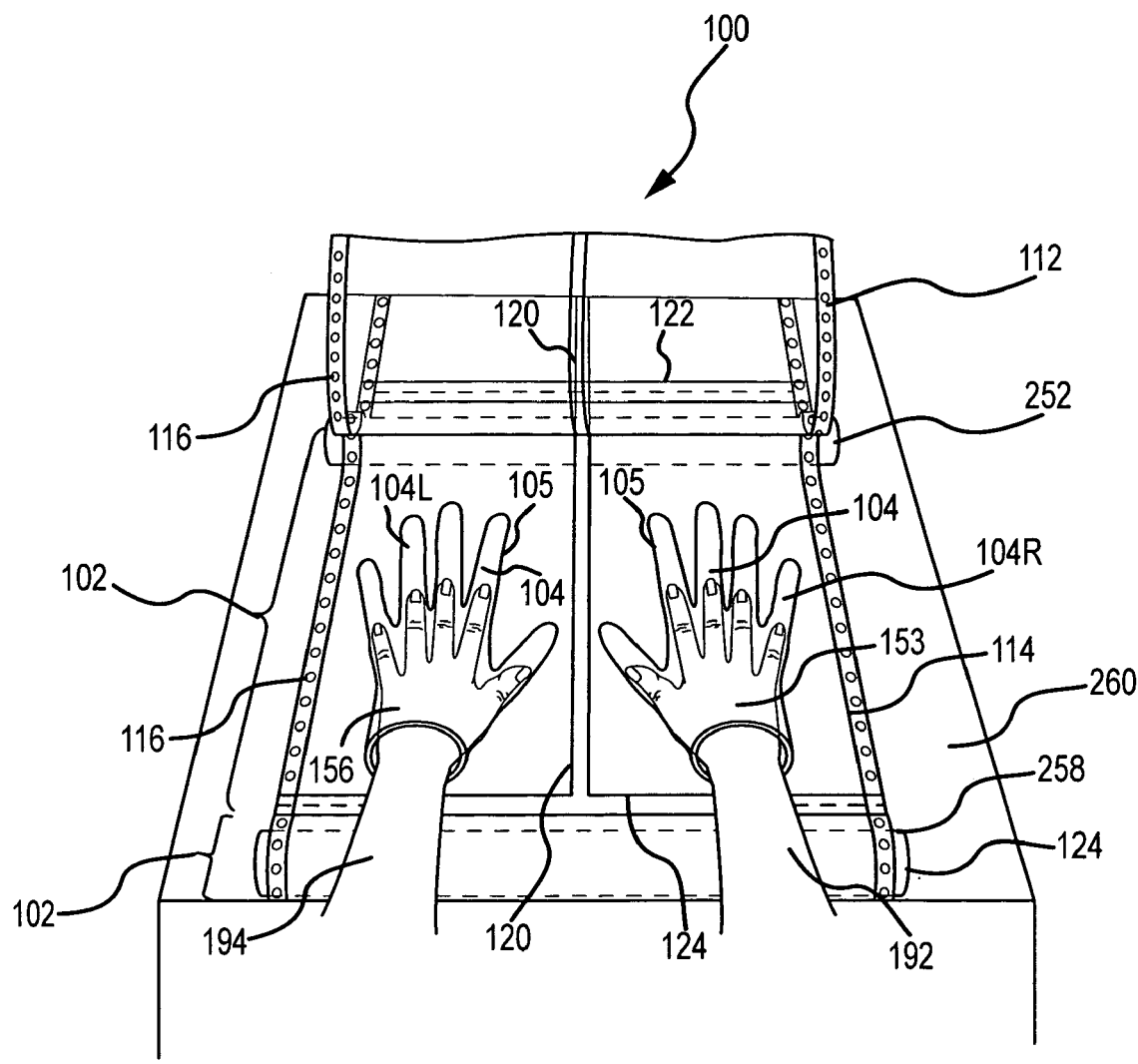
FIG. 5 is an illustration showing an embodiment of two-glove assembly and aspects of the manner in which a user would insert his hands into the gloves during a gloving operation.

FIG. 5 shows an embodiment of the assembly in FIG. 3 and complete separation of the upper layer from the rest of the package. The gloving package roll 100 is rolled on top of platen surface 260 between rear platen lower surface roller 252 and front platen lower surface roller 258 for the gloving operation. The wearer is shown by extending his left forearm 194 and right forearm 192 to place his left hand 156 and right hand 153 respectively in left glove 104L (Left) and right glove 104R (Right), extending his fingers to reach the glove finger 105 during the gloving operation.

Figure 6:
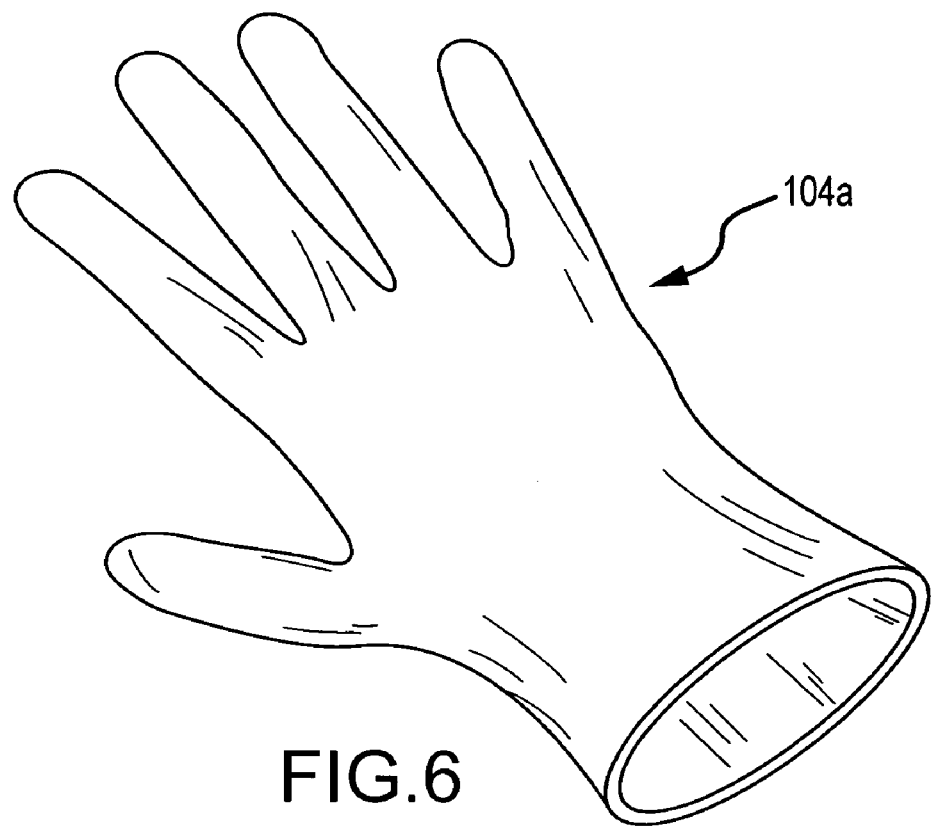
FIG. 6 is an illustration showing an embodiment of an elastic glove, such as a latex glove of the type used in medical offices and hospitals, which may be used with the invention.

FIG. 6 is an illustration showing an embodiment of an elastic glove 104a, such as a latex glove of the type used in medical offices and hospitals, which may be used with the invention. In one embodiment of the invention latex flexible gloves with thick cuffs are used; however, other embodiments are provided with conventional thickness gloves having a more or less uniform thickness throughout. Some embodiments of gloves have a rolled or thickened edge in the wrist area of the glove and are compatible for use with the inventive package and gloving machine.

Figure 7:
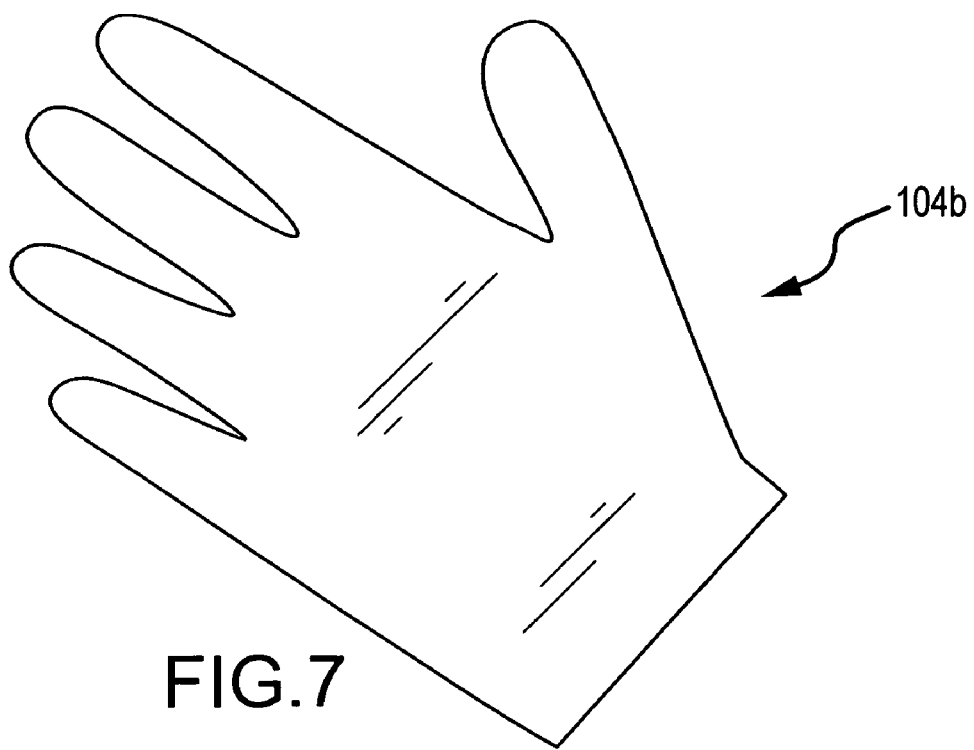
FIG. 7 is an illustration showing an embodiment of a flat glove, such as a vinyl or plastic glove, which is used for handling foods in food service operations.

FIG. 7 is an illustration of an embodiment of a flat glove 104b, such as a vinyl or plastic glove, which is used for handling foods in food service operations, and compatible for use with the inventive package and gloving machine.

FIG. 8 is an illustration showing an embodiment of a glove with a partial-loop or partial-hoop supportive glove-opening attachment strip 106 and dual-fasteners 108. The frontal view illustrates a glove with fasteners 108 on both sides holding the glove 104 onto glove pair bottom package layer 114 such that the attachment strip 106 is in a position to make the glove available for the wearer to put on in a gloving operation.

FIG. 9 is an illustration showing an embodiment of a glove 104 with a full-loop or full hoop supportive glove-opening attachment 106 and a single fastener 108. This frontal view illustrates a glove 104 with only one fastener 108 on the bottom of the glove 104 holding the glove onto glove pair bottom package layer 114 or onto single glove bottom package layer 144 such that the attachment strip 106 is in a position to make the glove available for the wearer to put on in a gloving operation.

FIG. 10 is an illustration showing a side view of an embodiment of structure and method for retaining the glove in a substantially flattened or low vertical profile stored position and then releasing a latch 107 from a latch holder 109 to permit the attachment strip 106 to open the wrist portion 104w of the glove in preparation for the gloving operation. FIG. 10a shows the glove in a latched configuration, FIG. 10b shows the glove as the latch 107 is being released by latch holder 109 and in an intermediate glove opening configuration, and FIG. 10c shows the glove in a complete open configuration during a gloving operation.

Figure 11A:
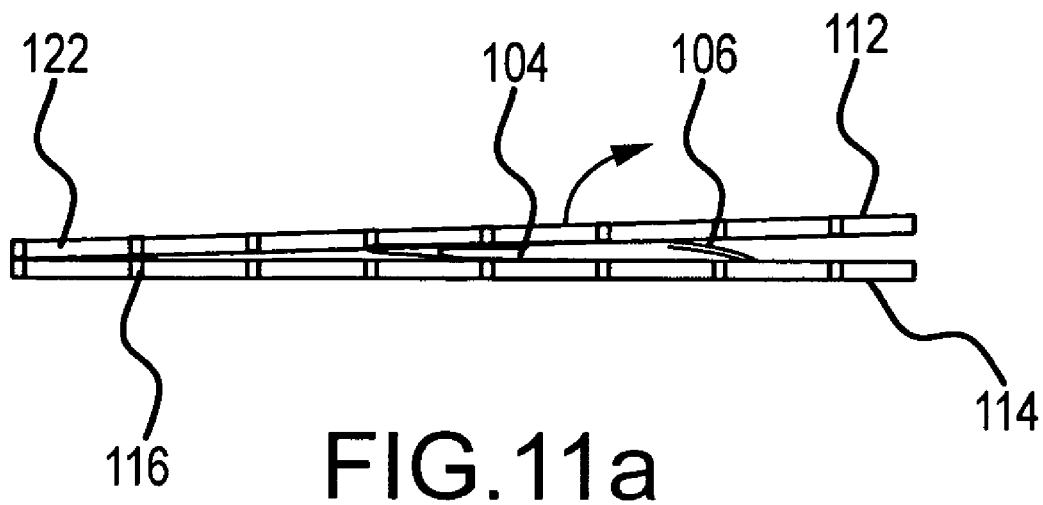
FIG. 11a shows a sectional view of the package with the upper and lower layers still enclosing the glove(s)
Figure 11B:
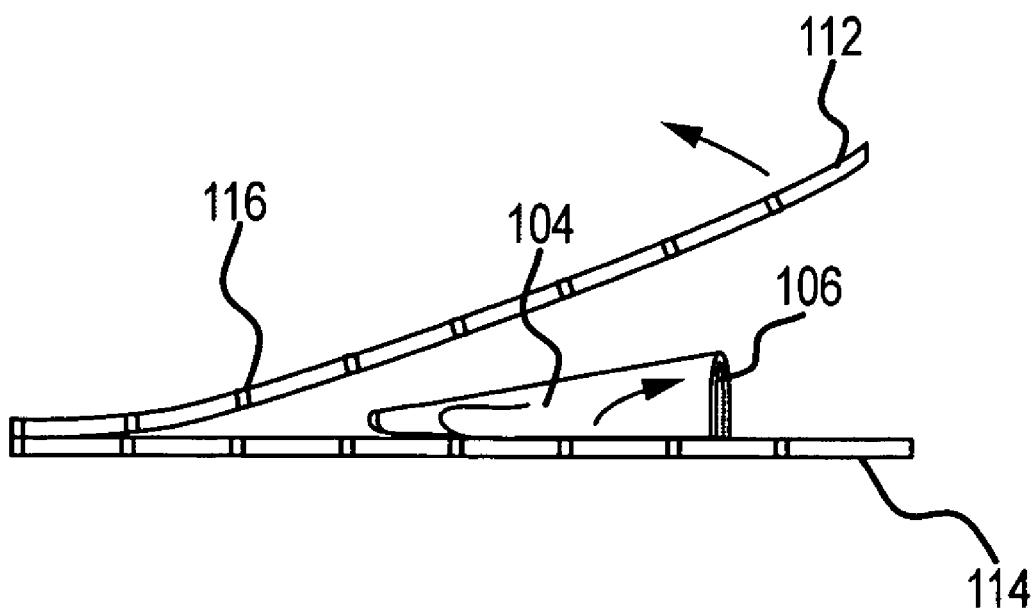
FIG. 11b shows the package as the layers are being separated in preparation for the gloving operation.

FIG. 11 is an illustration showing an embodiment of the glove package assembly 102 showing the separation of glove pair 104 top package layer 112 from the glove or gloves 104, as the glove package 102 moves through the gloving machine. FIG. 11a shows a sectional view of the package with glove pair top package layer 112 and glove pair bottom package layer 114 still enclosing the glove(s), and FIG. 11b shows the package 102 as the glove pair top package layer 112 and glove pair bottom package layer 114 are being separated in preparation for the gloving operation.

Figure 12:
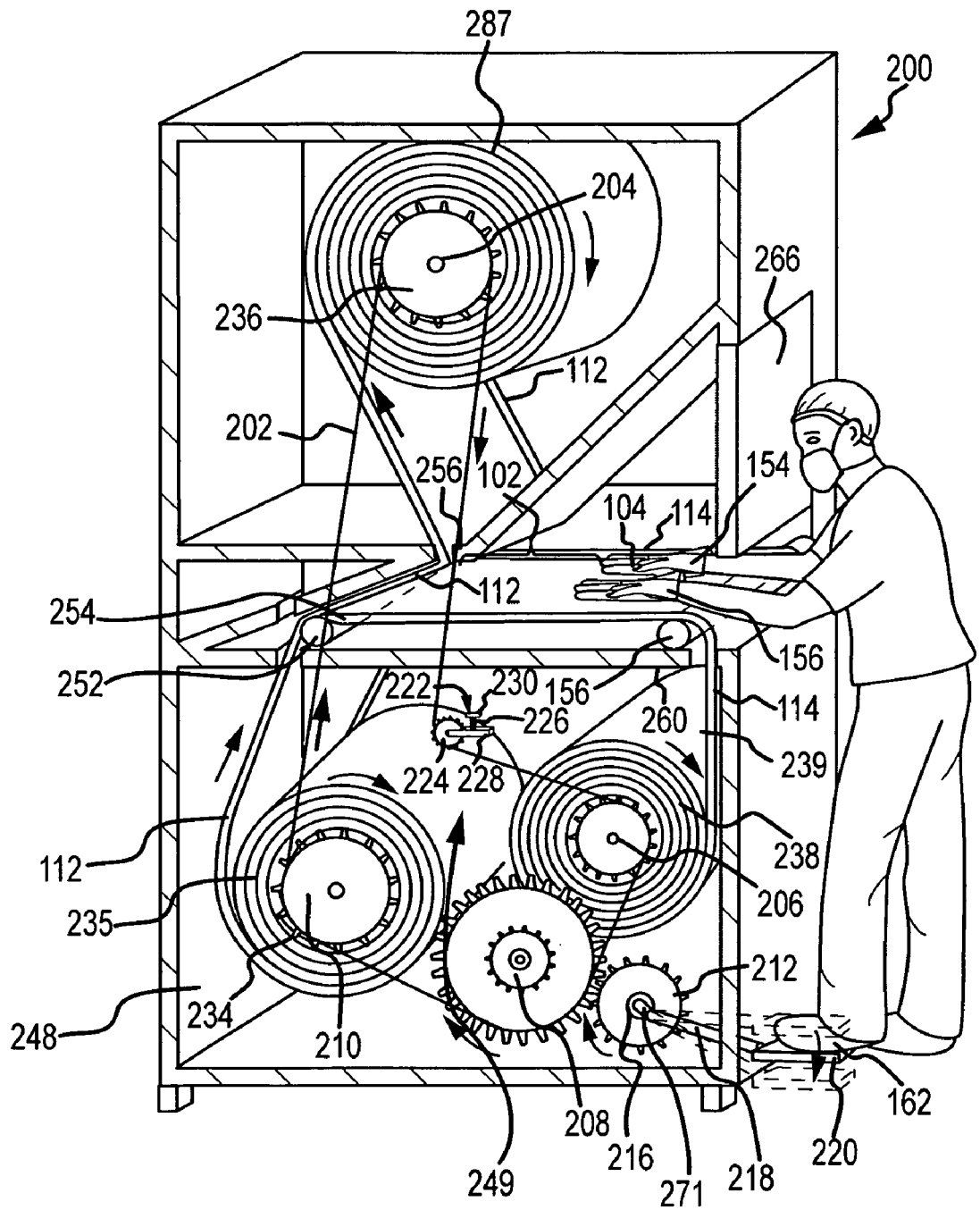
FIG. 12 is an illustration showing an embodiment of an exemplary gloving machine using rolled glove packages and a manual mechanical drive to move the glove packages through the machine.

FIG. 12 is an illustration showing an embodiment of an exemplary gloving machine 200 using rolled glove packages 102 and a manual mechanical drive 299 to move the glove packages through the machine.

As shown in this figure, the gloving machine 200 is comprised of a plurality of parts to provide for glove pair individual packet 102 or single glove individual packet 132 to unroll or unfold from storage region 298 of the machine and to be presented to the glove wearer 160 as the top portion 112 and bottom portion 114 unroll or unfold subsequently.

A foot pedal 220 (or other actuator) is mounted on to the frame of the gloving machine 200 and to the crank clutch assembly that has a one way latch 216 with a pedal pin 271 and is designed for operator foot 162 to press. The pressure from operator's foot 162 (or other body part) will force the drive gear 212 to turn driven gear 208 in a clockwise direction. A chain or belt 202 is placed around the driven gear 208, supply roll gear 210, top layer take-up gear (or pulley) 204 and bottom layer take-up gear (or pulley) 206 to rotate this assembly together in a clockwise direction when drive gear 212 turns during a gloving operation. Supply roll gear 210, top layer take-up gear (or pulley) 204 and bottom layer take-up gear (or pulley) 206 are respectively mounted to glove packet supply spool 234, top layer take-up spool 236 and bottom layer take-up spool 238. Glove packet supply spool 234, top layer take-up spool 236 and bottom layer take-up spool 238 are used respectively to hold glove packet supply roll 235, upper layer take-up roll 237 and lower layer take-up roll 239. When this assembly rotates, it feeds the glove packet supply roll 235 containing roles of glove pair pack 100 or single glove packet roll 130, depending on the embodiment used onto platen surface 260. For every gloving operation, lower layer take-up roll 239 and upper layer take up roll 237 will rotate to roll up glove pair bottom package layer 114 and glove pair top package layer 112 respectively. In addition, there may be an optional tensioner assembly 222 that is comprised of a tensioner gear 224 that is connected to the tensioner arm 228 and is engaged with the belt or chain 202 by a spring 226 that is attached to block 230 to provide for a tight grip of gears by the belt or chain 202.

According to one embodiment, the size and diameter of the driven gear 208, supply roll gear 210 and top layer take-up gear (or pulley) 204 are such that with one complete pressing of operator's foot 162, a complete glove pair individual packet 102 or single glove individual packet 132 will cover the platen surface 260 with glove pair top package layer 112 separated, and glove pair bottom package layer 114 of the previous sheet rolled on top of the lower layer take-up roll 239. In another embodiment, the size and diameters of the gears or pulleys are different and other means are provided to maintain proper feeding of the packages through the machine and tensioning on the web of material. In some embodiments, the foot pedal is connected to a ratcheting mechanism that permits the glove wearer to make multiple pedal pushes and incrementally advance the web of material to provide a fresh glove package at the gloving surface.

For each gloving operation, as the glove packet supply spool 234 turns, depending on the embodiment, a glove pair individual packet 102 or a single glove individual packet 132 is moved forward and the lower-upper layer splitter wedge 255 separates the glove pair top package layer 112 from the rest of the sheet. The glove pair top package layer 112 then rolls on top of rear upper surface roller 254 and slides over front upper surface roller 256 and gets rolled onto upper layer take up roll 237. This movement will in turn make the glove available and the wearer, by extending his left forearm 154 and right forearm 152, can place his left hand 156 and right hand 153, respectively, in left glove 104L and right glove 104R to receive gloves during a gloving operation. The glove pair bottom package layer of the previous glove pair individual packet 102 moves in parallel on top of front platen lower surface roller 258 and gets rolled on top of lower layer take-up roll 239. This cycle gets repeated for each gloving operation.

An optional transparent shield 266 is mounted on the body of the assembly vertically as a shield to separate the upper body of the operator 160 from glove rolls to protect internal parts of the machine from contamination from the environment and or from the operator 160, such as if the operator were to cough or sneeze. In one embodiment of the invention the gloving machine includes an air pump and intake filter, or a source of compressed gas and can provide a source of positive air pressure within the machine to further limit entry of contaminants.

Figure 13:
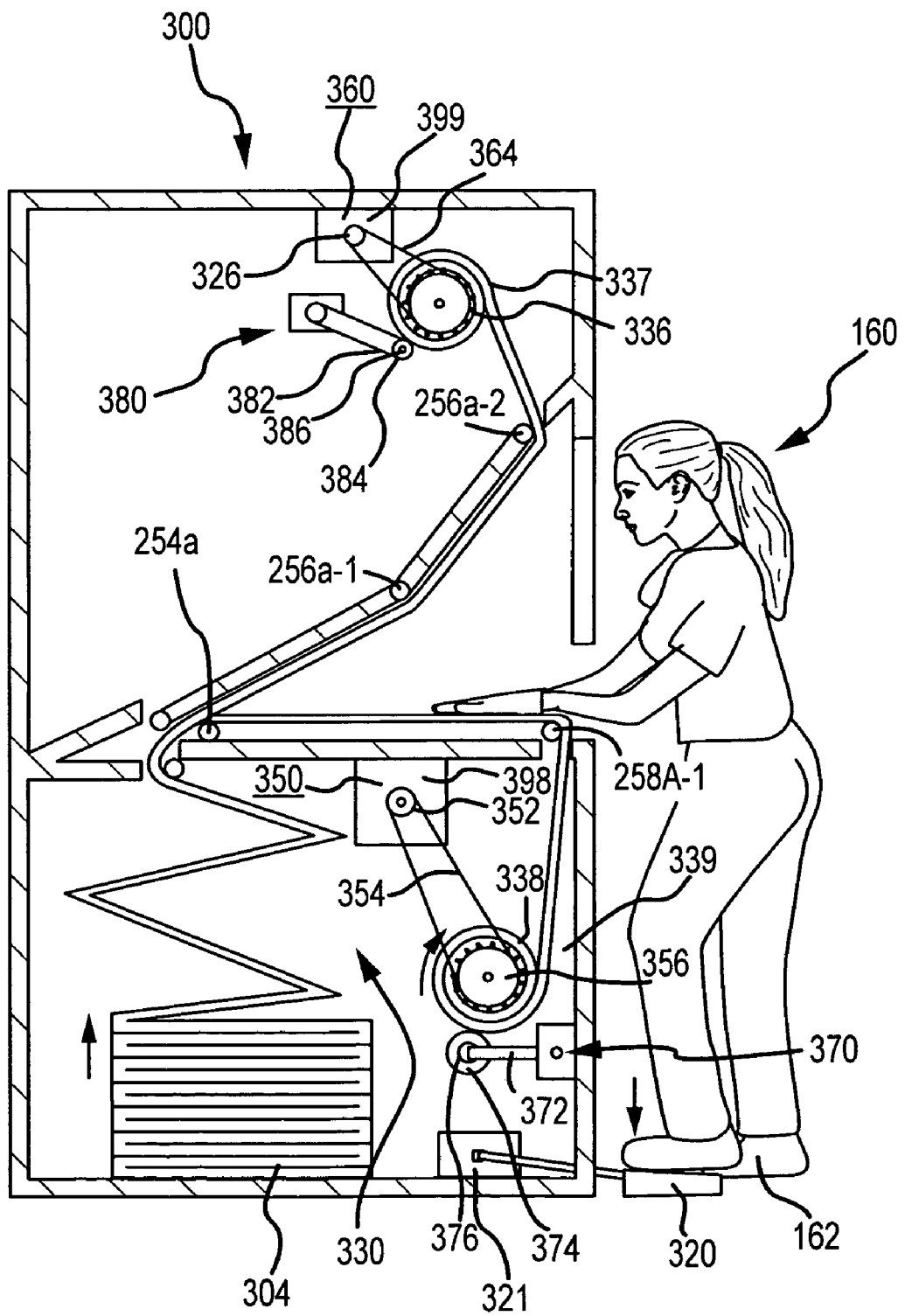
FIG. 13 is an illustration showing an embodiment of an exemplary gloving machine using pleated or folded glove packages and a motor driven mechanical drive to move the glove packages through the machine.

FIG. 13 is an illustration showing an embodiment of an exemplary gloving machine 300 using pleated or folded glove packages 304 and a motor driven mechanical drive 330 to move the glove packages 304 through the machine.

As shown in this figure, the gloving machine 300 is comprised of a plurality of parts to provide for glove pair individual packet 102 or single glove individual packet 132 to unfold from storage and to be presented to the glove wearer as the top and bottom portions unfold subsequently.

A foot actuator pedal 320 is connected to the actuator switch and motor control unit 321. It is designed for the operator's foot 162 to press. The pressure from operator foot 162 will activate the upper layer take-up spool motor and gear assembly 360 and lower layer take-up spool motor and gear assembly 350 simultaneously, forcing lower layer take-up spool drive gear (or pulley) 352 to turn the lower layer take up spool driven gear (pulley) 356 in a clockwise direction by rotating a lower layer take up spool drive chain (or belt) 354 that is placed around the lower layer take-up spool drive gear (pulley) 352 and lower layer take up spool driven gear (pulley) 356. When this assembly rotates, it feeds the stack of pleated gloves or glove pairs 304 containing rolls of glove pair pack 100 or single glove packet roll 130, depending on the embodiment used onto platen surface 260. For every gloving operation, lower layer take-up roll 339 and upper layer take up roll 337 will rotate together to roll up glove pair bottom package layer 114 and glove pair top package layer 112, respectively. In addition, there are two take-up roll pressure roller assemblies: lower layer take-up roll pressure roller assembly 370, and upper layer take-up roll pressure roller assembly 380. The lower layer take-up roll pressure roller assembly 370 is comprised of a lower roller 374 pushing against the lower layer take-up roll 339 to ensure a tight rolling motion and is connected to the lower arm 372. The lower arm is in turn connected to the pressure block 399 by an upper pivot 386. The upper layer take-up roll pressure roller assembly 380 comprises of an upper roller 384 pushing against the upper layer take-up roll 337 and it is connected to the upper arm 382. The upper arm is in turn connected to the pressure block 398 by an upper pivot 386.

The foot actuator switch and motor control unit 321 is designed such that with one complete pressing of operator's foot 162, a complete glove pair individual packet 102 or single glove individual packet 132 will cover the platen surface 260 with glove pair top package layer 112 separated, and glove pair bottom package layer 114 of the previous sheet rolled on top of the lower layer take-up roll 339. In another embodiment, a sensor is provided that operates in conjunction with markings or other indicia on the glove packages to automatically stop advance of the roll of packages when the glove package is positioned on the platen for a gloving operation.

For each gloving operation, as the stack of pleated gloves or glove pairs 304 feeds, depending on the embodiment, a glove pair individual packet 102 or a single glove individual packet 132 is moved forward onto platen surface 260. The lower-upper layer splitter wedge 397 separates glove pair top package layer 112 from the rest of the sheet and glove pair top package layer 112 rolls on top of rear upper surface roller 254a and slides over front upper surface rollers 256a-1 and 256a-2 and gets rolled onto upper layer take up roll 337. This movement makes the glove available, and the wearer by extending his left forearm 154 and right forearm 152, can place his left hand 156 and right hand 153 respectively in left glove 104L and right glove 104R to receive gloves during a gloving operation. The glove pair bottom package layer 114 of the previous glove pair individual packet 102 will move in parallel on top of front platen lower surface roller 258a-1 and gets rolled on top of lower layer take-up roll 339. This cycle may be repeated for each gloving operation.

A transparent shield 366 is mounted on the body of the assembly vertically as a shield to separate the upper body of the operator 160 from glove rolls to protect from contamination as described elsewhere herein.

Figure 14:
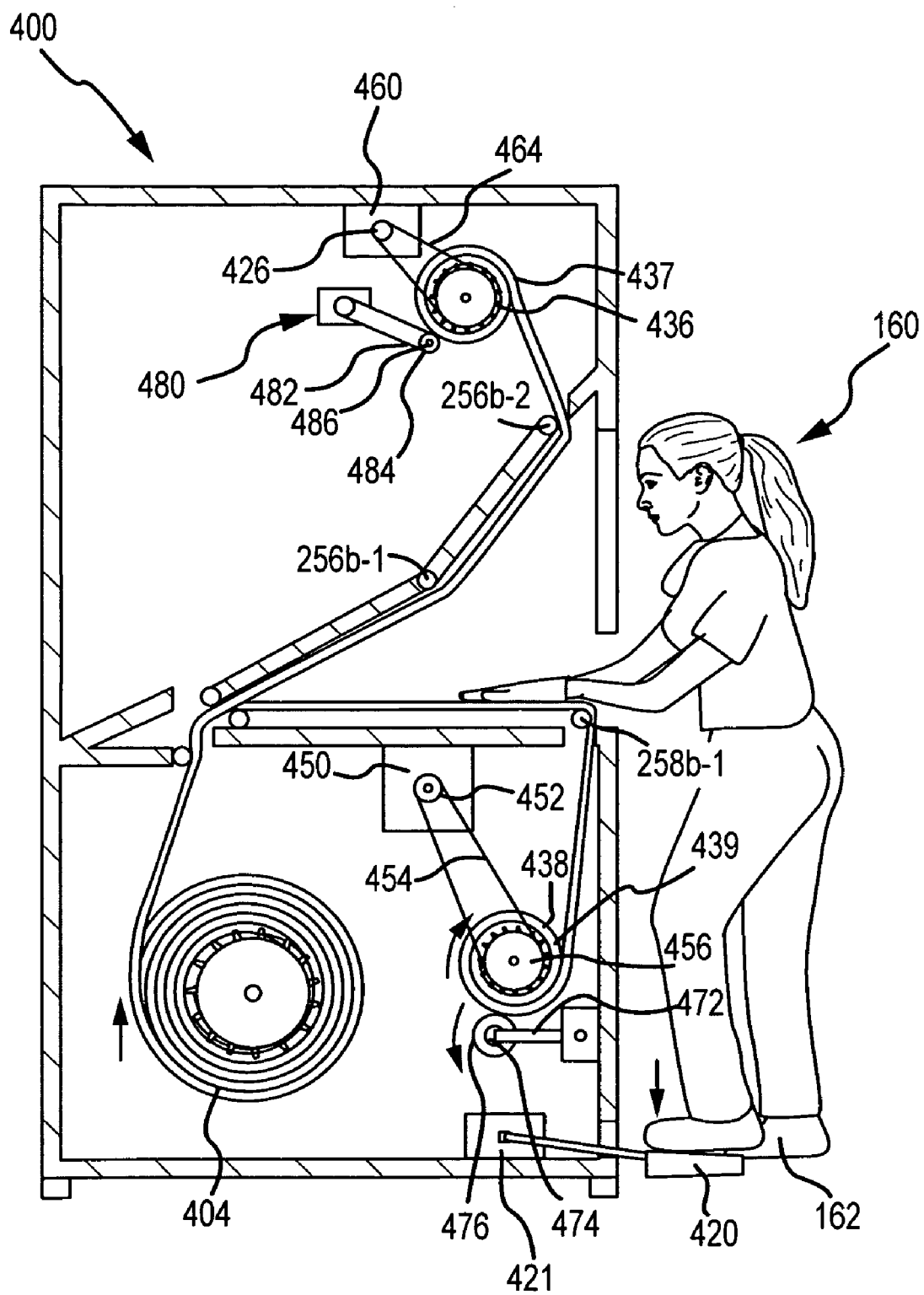
FIG. 14 is an illustration showing an embodiment of an exemplary gloving machine using rolled glove packages and a motor driven mechanical drive to move the glove packages through the machine.

FIG. 14 is an illustration showing an embodiment of an exemplary gloving machine using pleated or folded glove packages and a motor driven mechanical drive to move the glove packages through the machine.

As shown in this figure, the gloving machine 400 is comprised of a plurality of parts to provide for glove pair individual packet 102 or single glove individual packet 132 to unfold from storage and to be presented to the glove wearer as the top and bottom portions unfold subsequently.

A foot actuator pedal 420 is connected to the actuator switch and motor control unit 421. It is designed for the operator's foot 162 to press. The pressure from operator's foot 162 will activate the upper layer take-up spool motor and gear assembly 460 and lower layer take-up spool motor and gear assembly 450 simultaneously, forcing lower layer take-up spool drive gear (or pulley) 452 to turn the lower layer take up spool driven gear (pulley) 456 in a clockwise direction by rotating a lower layer take up spool drive chain (or belt) 454 that is placed around the lower layer take-up spool drive gear (pulley) 452 and lower layer take up spool driven gear (pulley) 456. When this assembly rotates, it feeds the glove packet supply role 404 containing rolls of glove pair pack 100 or single glove packet roll 130, depending on the embodiment used onto platen surface 260. For every gloving operation, lower layer take-up roll 439 and upper layer take up roll 437 will rotate in parallel to roll up glove pair bottom package layer 114 and glove pair top package layer 112, respectively. In addition, there are two take-up roll pressure roller assemblies: lower layer take-up roll pressure roller assembly 470 and upper layer take-up roll pressure roller assembly 480. The lower layer take-up roll pressure roller assembly 470 is comprised of a lower roller 474 pushing against the lower layer take-up roll 439 to ensure a tight rolling motion and is connected to the lower arm 472. The lower arm is in turn connected to the pressure block 499 by an upper pivot 486. The upper layer take-up roll pressure roller assembly 480 is comprised of an upper roller 484 pushing against the upper layer take-up roll 437 and is connected to the upper arm 482. The upper arm is in turn connected to the pressure block 498 by an upper pivot 486.

The foot actuator switch and motor control unit 421 is designed such that with one complete pressing of operator's foot 162, a complete glove pair individual packet 102 or single glove individual packet 132 will cover the platen surface 260 with glove pair top package layer 112 separated, and glove pair bottom package layer 114 of the previous sheet rolled on top of the lower layer take-up roll 439. In another embodiment, a sensor is provided that operates in conjunction with markings or other indicia on the glove packages to automatically stop advance of the roll of packages when the glove package is positioned on the platen for a gloving operation.

For each gloving operation, as the glove packet supply role 404 feeds on, depending on the embodiment, a glove pair individual packet 102 or a single glove individual packet 132 is moved forward onto platen surface 260. The lower-upper layer splitter wedge 497 separates glove pair top package layer 112 from the rest of the sheet and glove pair top package layer 112 rolls on top of rear upper surface roller 254*b* and slides over front upper surface rollers 256*b*-1 and 256*b*-2 and gets rolled onto upper layer take up roll 437. This movement makes the glove available and the wearer by extending his left forearm 154 and right forearm 152, can place his left hand 156 and right hand 153 respectively in 104L and 104R to receive gloves during a gloving operation. The glove pair bottom package layer 114 of the previous glove pair individual packet 102 will move in parallel on top of front platen lower surface roller 258*b*-1 and gets rolled on top of lower layer take-up roll 439. This cycle gets repeated for each gloving operation.

A transparent shield 466 is mounted on the body of the assembly vertically as a shield to separate the upper body of the operator 160 from glove rolls to protect from contamination as described elsewhere herein.

Figure 15:
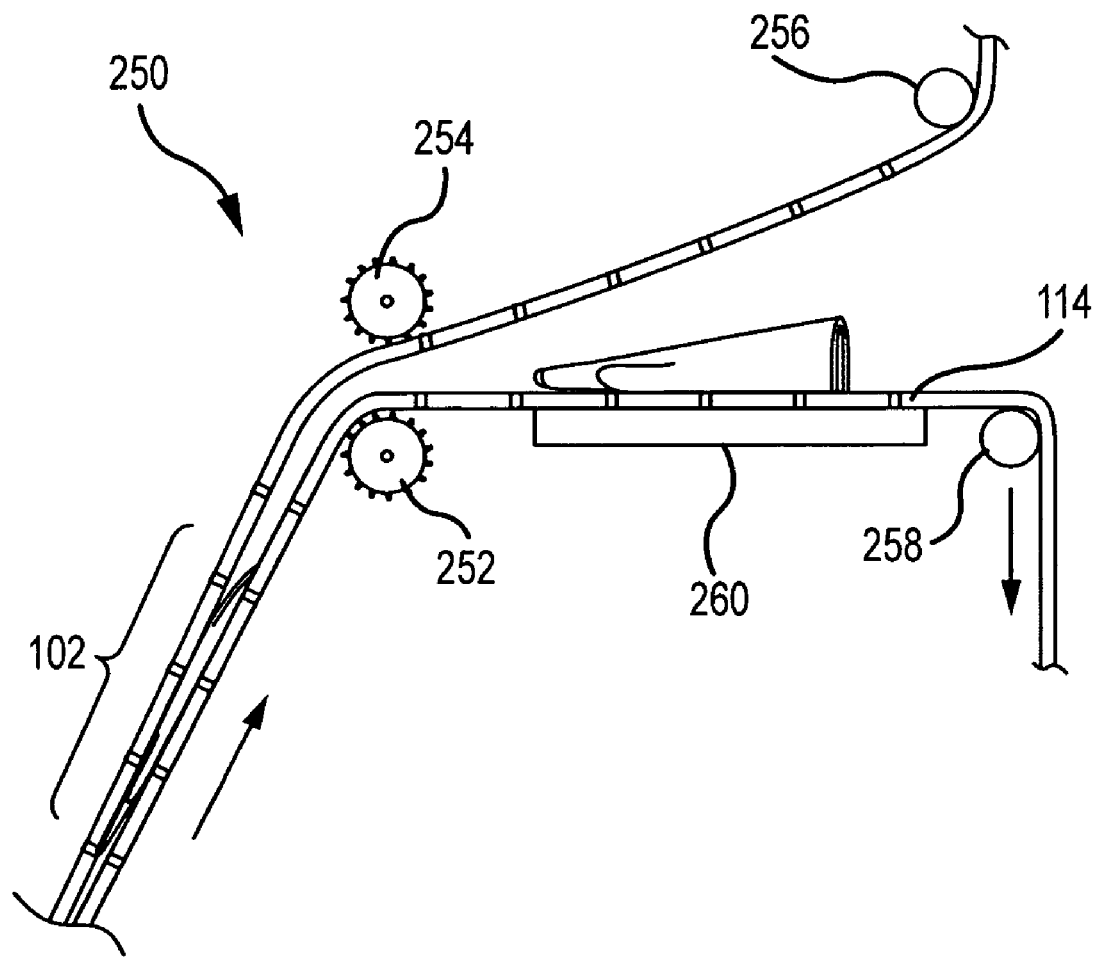
FIG. 15 is an illustration showing an embodiment of a glove separating mechanism as may be used in any of the gloving machines for separating the upper and lower layers of the glove packet from the gloves so that the gloves are available for gloving when presented at the gloving access point of the machine.

FIG. 15 is an illustration showing an embodiment of a glove separating mechanism which may be used in any of the gloving machines for separating the upper and lower layers of the glove from the gloves so that the gloves are available for gloving when presented at the gloving access point of the machine.

Figure 16:
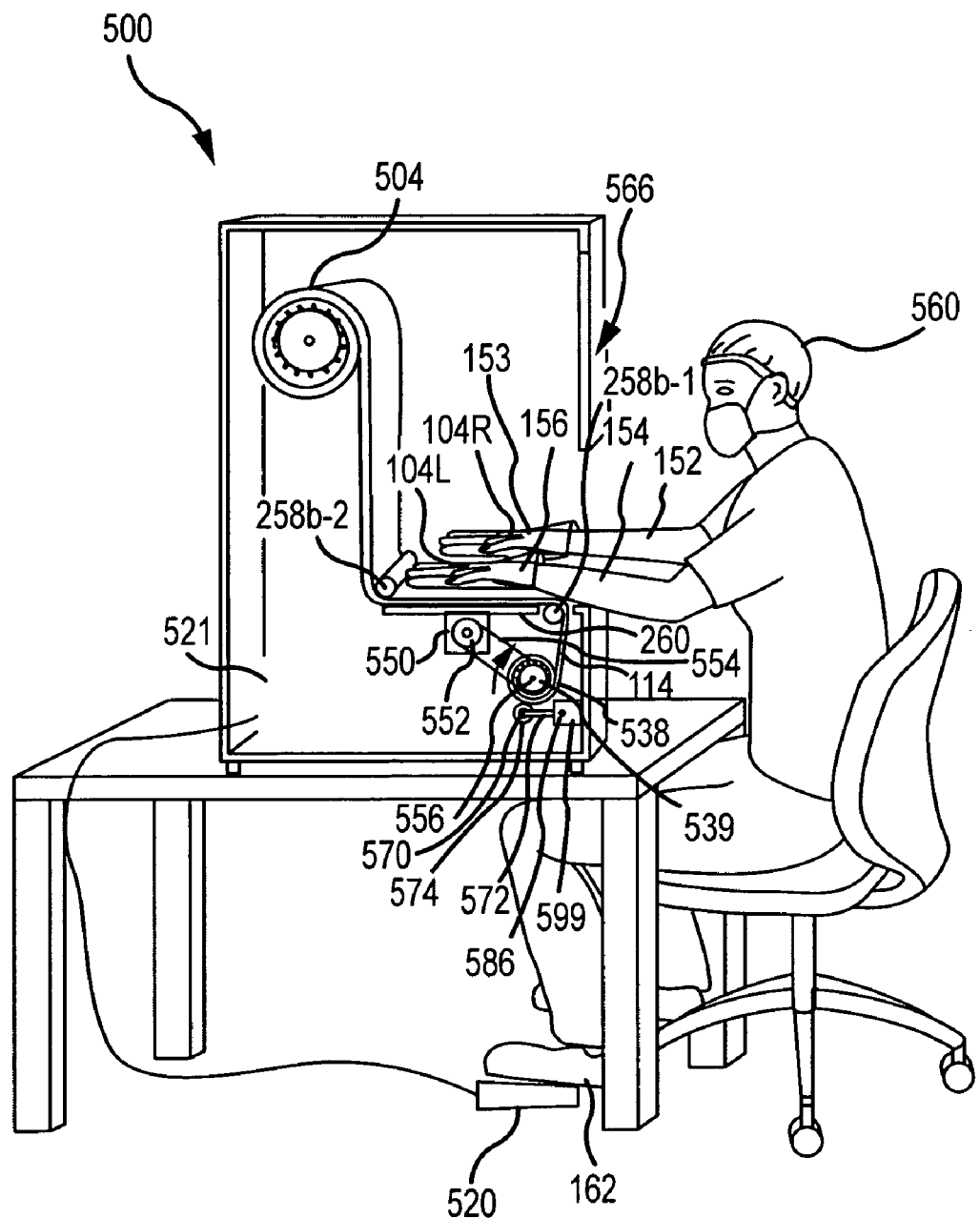
FIG. 16 is an illustration showing a portable embodiment of an exemplary gloving machine using pleated or folded glove packages and a motor driven mechanical drive to move the glove packages through the machine. This embodiment is sized such that it can be placed on top of a workbench rather than a stand-alone system.

FIG. 16 is an illustration showing a portable embodiment of an exemplary gloving machine using pleated or folded glove packages and a motor driven mechanical drive to move the glove packages through the machine. This embodiment is sized such that it can be placed on top of a workbench, counter, tabletop, or other surface rather than a stand-alone system. It may also be placed on a shelf or installed into or onto a wall.

As shown in this figure, the gloving machine 500 is comprised of a plurality of parts to provide for glove pair individual packet 102 or single glove individual packet 132 to unfold from storage and to be presented to the glove wearer as the bottom portion unfold subsequently.

A foot actuator pedal 520 is connected to the actuator switch and motor control unit 521. It is designed for the operator's foot 162 to press. Other actuators may alternatively be used such as for example a sensor or switch that may be actuated by the hand, wrist, forearm, or other body part. The pressure from operator's foot 162 (or other body part) will activate the lower layer take-up spool motor and gear assembly 550, forcing lower layer take up spool drive gear (or pulley) 552 to turn the lower layer take up spool driven gear (pulley) 556 in a clockwise direction by rotating a lower layer take up spool drive chain (or belt) 554 that is placed around the lower layer take-up spool drive gear (pulley) 552 and lower layer take up spool driven gear (pulley) 556. When this assembly rotates, it feeds the glove packet supply role 504 containing rolls of glove pair pack 100 or single glove packet roll 130, depending on the embodiment used onto platen surface 260. For every gloving operation, lower layer take-up roll 539 will rotate to roll up glove pair bottom package layer 114. In addition, there is a take-up roll pressure roller assembly, lower layer take-up roll pressure roller assembly 570. The lower layer take-up roll pressure roller assembly 570 is comprised of a lower roller 574 pushing against the lower layer take-up roll 539 to ensure a tight rolling motion and is connected to the lower arm 572. The lower arm is in turn connected to the pressure block 599 by an upper pivot 586.

The foot actuator switch 520 (or other actuating switch) and motor control unit 521 are designed such that with one complete pressing of operator's foot 162, a complete glove pair individual packet 102 or single glove individual packet 132 roll under rear upper surface roller 285-*b*2 and will cover the platen surface 260 with glove pair bottom package layer 114 of the previous sheet rolled on top of the lower layer take-up roll 539. In another embodiment, a sensor is provided that operates in conjunction with markings or other indicia on the glove packages to automatically stop advance of the roll of packages when the glove package is positioned on the platen for a gloving operation.

For each gloving operation, as the glove packet supply role 504 feeds on, depending on the embodiment, a glove pair individual packet 102 or a single glove individual packet 132 is moved forward onto platen surface 260. This movement makes the glove available and the wearer by extending his left forearm 154 and right forearm 152, can place his left hand 156 and right hand 153 respectively in 104L and 104R to receive gloves during a gloving operation. The glove pair bottom package layer 114 of the previous glove pair individual packet 102 will move on top of front platen lower surface roller 258b-1 and gets rolled on top of lower layer take-up roll 539. This cycle gets repeated for each gloving operation.

A transparent shield 566 is mounted on the body of the assembly vertically as a shield to separate the upper body of the operator 160 from glove rolls to protect from contamination as described elsewhere herein.

Having now described various facets and features of embodiments of the invention, now are disclosed additional particular embodiments of the invention.

In one embodiment, the invention provides a method of gloving a person, the method comprising the steps of: advancing a new package containing a pair of gloves including a first glove and a second glove attached to a web of material for transporting the package from a normally inaccessible storage location to a user accessible location within a housing of a gloving machine; opening the package as it is advanced through the gloving machine by removing an upper cover layer of material from the first and second gloves and from a base lower layer of material; presenting a first glove and a second glove on the lower base layer to within arms reach of the person to be gloved; substantially stabilizing the first glove in a physical position on a gloving surface so that the person can insert a first hand into an opening in the first glove without needing to touch or hold the outer surface of the first glove with a second hand; substantially stabilizing the second glove in a physical position on the gloving surface so that the person can insert the second hand into an opening in the second glove without needing to touch or hold the outer surface of the second glove with the first hand; and permitting detachment of the first and second gloves from the lower base layer of material to complete the gloving operation.

In another embodiment, this method provides that wherein the advancing of the new package from the storage location also advances a used package from which the first and second gloves where removed into a packaging take-up location within the housing of the gloving machine.

In another embodiment, this method provides that wherein the gloving machine includes a manual mechanical drive to advance the glove packages through the machine, and manual mechanical energy is input to the machine by the persons pressing a foot pedal.

In another embodiment, this method provides that wherein the gloving machine includes an electrical motor driven mechanical drive to advance the glove packages through the machine, and the electrical motor driven mechanical drive is activating by the person using a switch or lever.

In another embodiment, this method provides that wherein the gloving machine includes an air or fluid pressure motor driven mechanical drive to advance the glove packages through the machine, and the air pressure or fluid pressure driven mechanical drive is activating by the person using a switch or lever.

In another embodiment, this method provides that wherein the glove packages are stored within the gloving machine as folded pleated packages and pulled from a supply stack during the advancing.

In another embodiment, this method provides that wherein the glove packages are stored within the gloving machine as a roll of packages and pulled from a supply roll during the advancing.

In another embodiment, the invention provides a gloving machine for applying gloves to the hands of a person, the gloving machine comprising: an actuator mounted on to the frame of the gloving machine and to a crank clutch assembly operable to generate a movement upon receiving at least one foot press by the person; a drive assembly for advancing a package of gloves from a storage area to a gloving position accessible to the hands of the person to be gloved, the drive assembly including a drive gear or pulley connected to the crank clutch assembly to turn a driven gear, a chain or belt placed partially around the driven gear or pulley to produce a friction so that rotation of the driven gear or pulley will move the chain or belt, a supply roll gear, a top layer take-up gear, and a bottom layer take-up gear to rotate; the drive assembly supply roll gear and the top layer take-up gear and the bottom layer take-up gear respectively mounted to a glove packet supply spool, to a top layer take-up spool, and to a bottom layer take-up spool; the glove packet supply spool and the top layer take-up spool and the bottom layer take-up spool being operable respectively to hold a glove packet supply roll, to hold an upper layer take-up roll, and to hold a lower layer take-up roll; a lower-upper layer splitter wedge operable to separate a glove pair top package layer from a glove pair lower package layer; a rear upper surface roller, an upper surface roller, and a front platen lower surface roller mounted to a platen surface and operable during the advancing or the package of gloves for moving the lower package layer through the machine with a controlled amount of friction.

In another embodiment, this gloving machine may further include a transparent shield mounted on the body of the assembly to separate the upper body of the user from the glove packages and to protect internal parts of the machine from contamination from without the machine.

In another embodiment, this gloving machine may provide an air pump and intake filter or a source of compressed gas is utilized to provide a source of positive air pressure within the machine to further limit entry of contaminants.

In another embodiment, this gloving machine may further provide an optional tensioner assembly connected to a tensioner arm engaged with the belt or chain by a spring, the spring being attached to a support for maintaining tension of the belt or chain during operation.

In another embodiment, the gloving machine may further comprise a gloving package, wherein the gloving package is disposed internal to the gloving machine and comprises: a substantially planar sheet form bottom package layer; a glove pair including a first glove and a second glove arranges in side-by-side relationship; glove attachment means for detachably securing the glove pair to the bottom package layer; and a substantially planar sheet form top package layer overlying the glove pair and substantially secured and detachably sealed to the bottom package layer for containing the glove pair and maintaining a desired degree of sanitation or sterility.

In another embodiment, the invention provides a gloving machine for applying gloves, the gloving machine comprising: an actuator mounted on to a frame and to a motor control unit for operator foot to press; the actuator activating an upper layer take-up spool motor and gear assembly and a lower layer take-up spool motor and gear assembly, forcing a lower layer take-up spool drive gear (or pulley) turn a lower layer take up spool driven gear (or pulley) in a clockwise direction by rotating a lower layer take up spool drive chain (or belt) placed around the lower layer take up spool drive gear (pulley) and the lower layer take up spool driven gear (pulley); a lower-upper layer splitter wedge to separate a glove pair top package layer; a rear upper surface roller; an upper surface roller, and a front platen lower surface roller mounted on to a platen surface.

In another embodiment, this gloving machine may provide that wherein a transparent shield is mounted on the body of the assembly to separate the upper body of user from glove rolls to protect internal parts of the machine from contaminations.

In another embodiment, this gloving machine may provide wherein an air pump and intake filter, or a source of compressed gas is utilized to provide a source of positive air pressure within the machine to further limit entry of contaminants.

In another embodiment, this gloving machine may provide that wherein an optional tensioner assembly connected to a tensioner arm engaged with the belt or chain by a spring, the spring attached to a block for providing a tight grip of the gears by the belt or chain.

In another embodiment, the gloving machine may further comprise a gloving package, wherein the gloving package is disposed internal to the gloving machine and comprises: a substantially planar sheet form bottom package layer; a glove pair including a first glove and a second glove arranges in side-by-side relationship; glove attachment means for detachably securing the glove pair to the bottom package layer; and a substantially planar sheet form top package layer overlying the glove pair and substantially secured and detachably sealed to the bottom package layer for containing the glove pair and maintaining a desired degree of sanitation or sterility.

In another embodiment, the invention may provide a gloving package comprising: a substantially planar sheet form bottom package layer; a glove pair including a first glove and a second glove arranges in side-by-side relationship; glove attachment means for detachably securing the glove pair to the bottom package layer; and a substantially planar sheet form top package layer overlying the glove pair and substantially secured and detachably sealed to the bottom package layer for containing the glove pair and maintaining a desired degree of sanitation or sterility.

In another embodiment, this gloving package may further comprise: means for gripping the package and for urging the package through a gloving machine transport when the package is used in conjunction with an automatic gloving machine.

In another embodiment, this gloving package may provide a plurality of the gloving packages are connected to each other and at least one of the bottom package layer and the top package layer form or are connected to a web of material that serves at least in part to transport the glove packages.

In another embodiment, this gloving package may provide wherein the glove or the glove pairs are accompanied by an glove pair surround to carry the glove or the gloves and to assist at maintaining a relatively uniform package thickness between the glove or the gloves containing regions and non-glove containing regions.

In another embodiment, this gloving package may further comprise at least a partial loop supportive glove-opening attachment strip and dual fasteners for attaching the glove or gloves to a support layer.

In another embodiment, this gloving package may further comprise a full loop or full hoop supportive glove-opening attachment and a fastener for attaching the glove or gloves to a support layer.

In another embodiment, this gloving package may further comprise at least a partial loop supportive glove-opening attachment strip and dual fasteners for attaching the glove or gloves to a support layer.

In another embodiment, this gloving package may further comprise a full loop or full hoop supportive glove-opening attachment and a single faster for attaching the glove or gloves to a support layer.

In another embodiment, this gloving package may provide that wherein a plurality of glove pair individual packets are defined along a substantially continuous web or roll of material by glove pair roll tear perforations.

In another embodiment, this gloving package may provide wherein pleated glove packages are used for the gloving package.

In another embodiment, this gloving package may provide wherein rolled glove packages are used for gloving package.

In another embodiment, the invention provides a gloving machine for applying gloves to the hands of a person, the gloving machine comprising: a gloving region having a surface for supporting a packaged glove to a person, the gloving region accessible to the hand of the person to be gloved; and a glove package transport mechanism operative to retrieve at least one glove enclosed in a substantially sealed glove package from a storage region to the gloving region.

In another embodiment, this gloving machine may provide that the packaged gloves are stored external to a housing of the gloving machine.

In another embodiment, this gloving machine may provide that the packaged gloves are stored internal to a housing of the gloving machine.

In another embodiment, the invention provides a method of automatically dispensing gloves, the method comprising the steps of: transporting at least one packaged glove from a first storage region to a gloving region; opening the packaged glove to expose the glove to a person to be gloved; presenting the at least one packaged glove to the hand of a person to be gloved; and removing the empty glove package to a second storage region.

In another embodiment, this method may further comprise: repeating the transporting, opening, presenting, and removing steps to dispense a plurality of gloves.

In another embodiment, this method the gloves are provided as at least one glove package comprising: a substantially planar sheet form bottom package layer; a glove pair including a first glove and a second glove arranges in side-by-side relationship; glove attachment means for detachably securing the glove pair to the bottom package layer; and a substantially planar sheet form top package layer overlying the glove pair and substantially secured and detachably sealed to the bottom package layer for containing the glove pair and maintaining a desired degree of sanitation or sterility.

The foregoing description of the aspects of the present invention has been presented for purposes of illustration and description. It is not intended to be exhaustive or to limit the present invention to the precise form disclosed, and modifications and variations are possible in light of the above teachings or may be acquired from practice of the present invention. The principles of the present invention and its practical application were described in order to explain the to enable one skilled in the art to utilize the present invention in various embodiments and with various modifications as are suited to the particular use contemplated. Thus, while only certain aspects of the present invention have been specifically described herein, it will be apparent that numerous modifications may be made thereto without departing from the spirit and scope of the present invention.

I claim:

1. A gloving machine for applying gloves to the hands of a person, the gloving machine comprising:
an actuator mounted on to a frame of the gloving machine and to a crank clutch assembly operable to generate a movement upon receiving at least one foot press by the person;
a drive assembly configured to advance a package of gloves from a storage area to a gloving position accessible to the hands of the person to be gloved, the drive assembly including a drive gear or pulley connected to the crank clutch assembly to turn a driven gear and a chain or belt placed partially around the driven gear or pulley to produce a friction so that rotation of the driven gear or pulley will cause the chain or belt, a drive assembly supply roll gear, a top layer take-up gear, and a bottom layer take-up gear to rotate;
the drive assembly supply roll gear mounted to a glove packet supply spool, the top layer take-up gear mounted to a top layer take-up spool, and the bottom layer take-up gear mounted to a bottom layer take-up spool;
the glove packet supply spool operable to hold a glove packet supply roll, the top layer take-up spool operable to hold an upper layer take-up roll, and the bottom layer take-up spool being operable to hold a lower layer take-up roll;
a layer splitter wedge operable to separate a glove pair top package layer from a glove pair lower package layer; and
a rear upper surface roller, an upper surface roller, and a front platen lower surface roller mounted to a platen surface and operable during the advancing of the package of gloves for moving the glove pair lower package layer through the machine with a controlled amount of friction;
wherein an air pump and intake filter or a source of compressed gas is utilized to provide a source of positive air pressure within the machine to further limit entry of contaminants.

2. The gloving machine of claim 1, further comprising a transparent shield mounted on the body of the assembly to separate the upper body of the user from the glove packages and to protect internal parts of the machine from contamination.

3. The gloving machine of claim 1, further comprising
a gloving package, wherein the gloving package is disposed internal to the gloving machine and comprises a substantially planar sheet form bottom package layer;
a glove pair including a first glove and a second glove arranged in side-by-side relationship;
glove attachment means for detachably securing the glove pair to the bottom package layer; and
a substantially planar sheet form top package layer overlying the glove pair and substantially secured and detachably sealed to the bottom package layer for containing the glove pair and maintaining a desired degree of sanitation or sterility.

4. A gloving machine for applying gloves to the hands of a person, the gloving machine comprising:
an actuator mounted on to a frame of the gloving machine and to a crank clutch assembly operable to generate a movement upon receiving at least one foot press by the person;
a drive assembly configured to advance a package of gloves from a storage area to a gloving position accessible to the hands of the person to be gloved, the drive assembly including a drive gear or pulley connected to the crank clutch assembly to turn a driven gear and a chain or belt placed partially around the driven gear or pulley to produce a friction so that rotation of the driven gear or pulley will cause the chain or belt, a drive assembly supply roll gear, a top layer take-up gear, and a bottom layer take-up gear to rotate;
the drive assembly supply roll gear mounted to a glove packet supply spool, the top layer take-up gear mounted to a top layer take-up spool, and the bottom layer take-up gear mounted to a bottom layer take-up spool;
the glove packet supply spool operable to hold a glove packet supply roll, the top layer take-up spool operable to hold an upper layer take-up roll, and the bottom layer take-up spool being operable to hold a lower layer take-up roll;
a layer splitter wedge operable to separate a glove pair top package layer from a glove pair lower package layer; and
a rear upper surface roller, an upper surface roller, and a front platen lower surface roller mounted to a platen surface and operable during the advancing of the package of gloves for moving the glove pair lower package layer through the machine with a controlled amount of friction;
wherein a tensioner assembly is connected to a tensioner arm engaged with the belt or chain by a spring, the spring attached to a support for maintaining tension of the belt or chain during operation.

5. A gloving machine for applying gloves, the gloving machine comprising:
an actuator mounted on to a frame and to a motor control unit configured for an operator foot to press, the actuator activating an upper layer take-up spool motor and gear assembly and a lower layer take-up spool motor and gear assembly, forcing a lower layer take-up spool drive gear or pulley to turn a lower layer take up spool driven gear or pulley in a clockwise direction by rotating a lower layer take up spool drive chain or belt positioned around the lower layer take up spool drive gear or pulley and the lower layer take up spool driven gear or pulley;
a layer splitter wedge to separate a glove pair top package layer;
a rear upper surface roller;
an upper surface roller; and
a front platen lower surface roller mounted on to a platen surface,
wherein an air pump and intake filter or a source of compressed gas is utilized to provide a source of positive air pressure within the machine to further limit entry of contaminants.

6. The gloving machine of claim 5, wherein a transparent shield is mounted on the body of the assembly to separate the upper body of a user from glove rolls to protect internal parts of the machine from contaminations.

7. The gloving machine of claim 5, wherein a tensioner assembly is connected to a tensioner arm engaged with the belt or chain by a spring, the spring attached to a block for providing a tight grip of the gears by the belt or chain.

8. The gloving machine of claim 5, further comprising
a gloving package, wherein the gloving package is disposed internal to the gloving machine and comprises a substantially planar sheet form bottom package layer;
a glove pair including a first glove and a second glove arranged in side-by-side relationship;
glove attachment means for detachably securing the glove pair to the bottom package layer; and
a substantially planar sheet form top package layer overlying the glove pair and substantially secured and detachably sealed to the bottom package layer for containing the glove pair and maintaining a desired degree of sanitation or sterility.

9. The gloving machine of claim 4, further comprising a transparent shield mounted on the body of the assembly to separate the upper body of the user from the glove packages and to protect internal parts of the machine from contamination.

10. The gloving machine of claim 4, further comprising a gloving package, wherein the gloving package is disposed internal to the gloving machine and comprises a substantially planar sheet form bottom package layer;

a glove pair including a first glove and a second glove arranged in side-by-side relationship;

glove attachment means for detachably securing the glove pair to the bottom package layer; and a substantially planar sheet form top package layer overlying the glove pair and substantially secured and detachably sealed to the bottom package layer for containing the glove pair and maintaining a desired degree of sanitation or sterility.

* * * * *